US007012154B2

(12) United States Patent
Vineyard et al.

(10) Patent No.: US 7,012,154 B2
(45) Date of Patent: Mar. 14, 2006

(54) CONTINUOUS PROCESS FOR ON-SITE AND ON-DEMAND PRODUCTION OF AQUEOUS PERACTEIC ACID

(75) Inventors: Mark K. Vineyard, Houston, TX (US); Robert L. Moison, Apple Valley, MN (US); Frederic E. Budde, Eagan, MN (US); John R. Walton, Colfax, CA (US)

(73) Assignee: Peragen Systems, LLC, Eagan, MN (US)

( * ) Notice: Subject to any disclaimer, the term of this patent is extended or adjusted under 35 U.S.C. 154(b) by 0 days.

(21) Appl. No.: 10/900,209

(22) Filed: Jul. 28, 2004

(65) Prior Publication Data

US 2006/0025627 A1    Feb. 2, 2006

(51) Int. Cl.
*C07C 409/24*    (2006.01)
*C01B 15/00*    (2006.01)
(52) U.S. Cl. ..................................... 562/6; 252/186.26
(58) Field of Classification Search ................ 562/6; 252/186.26
See application file for complete search history.

(56) References Cited

U.S. PATENT DOCUMENTS

| 3,264,346 | A | 8/1966 | Weilberg |
| 5,122,538 | A | 6/1992 | Lokkesmoe et al. |
| 5,683,724 | A | 11/1997 | Hei et al. |
| 5,886,216 | A | 3/1999 | Pudas |
| 2002/0177732 | A1 | 11/2002 | Pohjanvesi et al. |
| 2002/0193626 | A1 | 12/2002 | Pohjanvesi et al. |
| 2005/0014970 | A1 | 1/2005 | Maata et al |

FOREIGN PATENT DOCUMENTS

| EP | 1004576 A1 | 5/2000 |
| EP | 0789016 B2 | 6/2001 |
| EP | 1247802 A1 | 10/2002 |

OTHER PUBLICATIONS

Liberti et al, Water Science and Technology, Comparison of Advanced Disinfecting Methods for Municipal Wastewater Reuse in Agriculture, 2000, 42(1-2), pp. 235-245.*
"Methods of Preparation and Analysis of Organic Peroxy Acids," pp. 482-485.
Chadwick, AF/sjh, "Information for Design of an Aqueous Peracetic Acid Facility," Feb. 2, 1965 17 pages.
FMC "Technical Data," Report No. P-106-S, 1985, pp. 1-9.

"The Operation of a Bench Scale Peracetic Acid Generator and Typical Applications of Generator Peracid," FMC Corporation, 1963, pp. 1-16.
Swern, Daniel, Dr., "A New Continuous Process for Peracetic Acid Manufacture and Epoxidation,", Solvay Process Division of Allied Chemical Corporation, Technical Service Report No. 1.61, Sep. 9, 1961, 38 pages.
Swern, Daniel, "Organic Peroxides, vol. 1," pp. 340 to 353, and 460 to 475, Wiley Interscience.
Caddell, J.R., and Hurt, D.M., "Principles of Reactor Design, Homogeneous Reactions," Jul. 1951, pp. 333-338, vol. 47, No. 7.
Corrigan, T.E. and Young, E.F., "Chemical Engineering Fundamentals, General Considerations in Reaction Design-1," 2 pages.
Wilson, K.B., B.Sc., Ph.D. "Tubular Reactors, Part I. Calculation and Analysis of Longitudinal Temperature Gradients in Tubular Reactors," Sep. 28, 1946, 1 page.
Eakman, J.M., "Chemical Reactor Analysis (Part II)," Interoffice letter dated Jul. 7, 1964, 1 page.
Corrigan, T.E., "Chemical Engineering Fundamentals, Introduction to Reaction Kinetics," pp. 230-232.
Alves, George E., "Cocurrent liquid-gas flow in a pipe-line contactor," Chemical Engineering Progess, p. 449, vol. 50, No. 9.
Danos, Robert J., "Pipe reactor making diammonium phosphate now," Process Tehcnology, 1 page.
Jordan, Donald G., Ph.D., P.E., "Chemical Process Development, Part 1," 1968, p. 218.
Carberry, James J., "Chemical and Catalytic Reaction Engineering," p. 74.
Peracetic Acid (CAS No. 79-21-0) and its Equilibrium Solutions, JACC No. 40, pp. 2-3.
On the Other Hand, our Routing Switchers Handle Growth Very Nicely, L 10791, 3M, 1 page.

* cited by examiner

*Primary Examiner*—Paul A. Zucker
(74) *Attorney, Agent, or Firm*—Banner & Witcoff, Ltd.

(57) ABSTRACT

Peracetic acid in aqueous liquid solution or vapor phase is prepared on-site and on-demand in a continuous process. Peracetic acid can be produced at a controlled rate to meet the demands of a downstream operation. In one embodiment, a pipe-line reactor and distillation column is used for the production of peracetic acid. In another embodiment, an apparatus includes a continuous pot reactor and distillation column for producing peracetic acid. The present invention has the potential of providing a much safer source of aqueous peracetic acid than currently available processes, due in part to the limited inventories of reactants in the reactor, particularly those in the vapor phase.

51 Claims, 3 Drawing Sheets

CONTINUOUS PROCESS FOR ON-SITE AND ON-DEMAND PRODUCTION OF AQUEOUS PERACTEIC ACID

FIELD OF THE INVENTION

The present invention is directed to the preparation of aqueous peracetic acid, a useful oxidizing agent for such applications as disinfection, sterilization, bleaching, and chemical synthesis.

BACKGROUND OF THE INVENTION

Peracetic acid (denoted PAA or HOOAc herein) has long been recognized for its utility in a wide variety of end uses. In water and wastewater disinfection, for example, PAA destroys microorganisms and pathogens harmful to the public and the environment without producing toxic by-products or leaving chemical residuals. In bleaching applications, PAA yields higher levels of brightness without degrading fiber strength. Other applications, including equipment sanitizing, grain and soil sterilization, and chemical synthesis profit from the benefits of PAA over the alternatives.

PAA is currently produced commercially as an equilibrium mixture of hydrogen peroxide, acetic acid, water, and sulfuric acid with trace amounts of stabilizers (denoted equilibrium peracetic acid, or eq-PAA herein). The active peracetic acid content is typically controlled from 5 to 35%, by weight, depending on the particular end use.

However, there are several shortcomings with eq-PAA that limit its practical utility. For example, the use of eq-PAA is limited by its inherent instability and safety considerations, particularly at high concentrations. Thirty-five percent (35%) solutions are flammable under the National Fire Prevention Association (NFPA) standards. Commercial transport regulations restrict the concentration to less than 35% when shipped over public avenues, however, manufacturers typically limit the concentration to 15% except for special circumstances.

As an equilibrium product, Eq-PAA contains substantial quantities of unreacted raw materials. These unreacted materials represent economic waste that can increase the cost for the active PAA by a factor of two to three.

There are many applications where the presence of these unreacted materials discourages the use of eq-PAA. For example, in conventional wastewater treatment plants the unreacted hydrogen peroxide ($H_2O_2$) and acetic acid (HOAc) will contribute significantly to the loading properties in final discharges, including toxicity, Chemical Oxidation Demand (COD), Biochemical Oxygen Demand (BOD), and Total Organic Carbon (TOC), etc., all of which must meet local and federal discharge permits (for example NPDES, National Pollutant Discharge Elimination System) promulgated under the United States Of America Clean Water Act.

Several methods have been proposed to moderate the limitations of eq-PAA. In U.S. Pat. No. 5,122,538 to Lokkesmore et al., a method is disclosed to produce equilibrium peracetic acid products on-site at the point of use. The method utilizes a non-swelling acid exchange resin as a catalyst to produce peracetic acid from acetic acid and hydrogen peroxide. A drawback to this method is the peracetic acid product contains substantial amounts of acetic acid and hydrogen peroxide. The prolonged equilibration time (several hours) necessitates large inventories of peracetic acid that present additional storage hazards requiring special precautions. This method for on-site production and storage retains the adverse impacts on cost, safety and the environment.

A more complete solution involves separating and recycling the non-PAA components in eq-PAA. Among these is distilled PAA (denoted aq-PAA herein) which has been available since the 1950's.

In an early U.S. Pat. No. 3,264,346 to Weiberg, et al., a process is described for producing an aqueous solution of peracetic acid by distilling off the solution from a reaction medium containing acetic acid, hydrogen peroxide, sulfuric acid, water and peracetic acid. The use of this process calls for a molar ratio of hydrogen peroxide to acetic acid of from 5:1 to 15:1.

In Swern, D., "Organic Peroxides", Vol. 1, John Wiley & Sons, New York, 1970, pp. 349–351, a process is described for the production of peracetic acid by distilling off peracetic acid from an aqueous reaction medium containing acetic acid, hydrogen peroxide, peracetic acid, and sulfuric acid catalyst in substantial equilibrium.

Other art describes specific aspects of the aq-PAA production process such as distillation, purge disposal, and product stabilization.

One example of the distillation aspect is U.S. Pat. No. 5,886,217 to Pudas, which describes the production of eq-PAA and distilling off aq-PAA continuously based on the amount of thermal energy applied to the reaction medium. The purpose is to produce the maximum yield of aq-PAA from a commercial production viewpoint by increasing or maintaining a high level of thermal energy input.

In EP 0789016, a method is disclosed for producing peracetic acid by reacting hydrogen peroxide and acetic acid in an aqueous medium that is continuously supplied with more than 0.2 KW/kg of thermal energy while the peracetic acid produced is continuously separated and removed by distillation. The reaction medium circulates in the heating device with the aid of a pump, which increases the pressure of the reaction medium to allow temperature rise with boiling in the circulation loop.

Pudas U.S. Pat. No. 5,886,217 also describes a heat exchanger circulating device to supply the thermal energy to the reaction medium. A drawback to this method is that the heat exchanger circulating device circulates the reaction medium up to 200 times per hour and basically serves as a continuously mixed reactor and heater.

In EP 1004576 A1, a method is disclosed for producing peracetic acid by reacting hydrogen peroxide and acetic acid in an aqueous medium in the presence of an acid catalyst and continuously distilling off the peracetic acid, the molar ratio of hydrogen peroxide to acetic acid in the reaction medium ranging from 0.6:1 to 4:1, respectively, and the reaction medium being circulated through a thermosyphon reboiler by natural convection boiling.

Another derivation involves reaction medium sparging, wherein fresh acid catalyst is fed continuously into the reaction medium while withdrawing a similar volume continuously to purify the medium of impurities threatening the safety of the process. One example of medium sparging is described in U.S. patent application No. 20020177732 to Pohjanvesi, et al., which describes improvements by feeding the catalyst continuously into the reaction medium by withdrawing a portion of the medium as a bottom product. The resulting medium is distilled into aq-PAA at maximum yields.

EP 1247802 describes a method for disposing of the acid purge stream by neutralizing the remaining sulfuric acid and acetic acid therein and combining the stream with the distilled peracetic acid product. A slightly better utilization of the raw materials is achieved in addition to eliminating a waste stream.

Another example is EP 98203946.3, which additionally describes the use of stabilizers and chillers to stabilize the aq-PAA.

Another example is described in U.S. patent application No. 20020193626 to Pohjanvesi, et al., which describes using a base to neutralize the unreacted acids whereby the distilled PAA product is stabilized. Significantly, all these acid neutralization processes suffer from common drawbacks, including the addition of a stoichiometric equivalent amount of base and the introduction of conjugate salts that are not desirable in most applications.

The inherent instability of PAA leads to another shortcoming of aq-PAA: its transportability. When stored at ambient temperatures (for example 20° C.), aq-PAA quickly reverts to $H_2O_2$ and HOAc (approximately 1.5% decomposition per day). When stored at low temperatures (for example 0° C.), the reverse reaction is considerably slower and the product may retain a reasonable shelf life (approximately 0.3% decomposition per day). Thus, aq-PAA is not sufficiently stable for prolonged periods without elaborate refrigeration equipment and controls, which greatly complicates its distribution and storage.

To date, the United States Department of Transportation (USDOT) has not permitted the transportation of eq-PAA in containers greater than 300 gallon intermediate bulk containers (IBC's), while regulations for the transport of aq-PAA have not been delineated. Therefore, PAA cannot be shipped in bulk quantities and at prices competitive with conventional bulk chemicals such as sodium hypochlorite for disinfection.

In summary, the prior art related to aq-PAA production is concerned with producing both the highest yields of PAA and addressing the stability of PAA during production, handling, and storage regardless of the end use requirements.

Further, to date aq-PAA production technology has been applied commercially only within specialized chemical manufacturing facilities. These processes are designed for large scale production of PAA using large quantities of reacting solutions and large head spaces above the solution at the base of the distillation column. The principal hazard associated with the technology is the potential for unstable conditions (possible vapor phase explosions) to exist within the vapor space above the surface of the liquid in the reactor.

Thus, none of the described prior art teaches of a small to medium scale process suitable for practical on-site production of aq-PAA (i.e., one dedicated to specific end-use applications). There remains a need for a safer and more cost effective method for producing and applying PAA into various applications without releasing significant waste products. It would be especially desirable to develop a continuous process capable of producing aq-PAA with variable on-demand controls to suit a wide variety of applications, especially a process that can operate safely and efficiently under a range of processing conditions and with minimal human intervention.

BRIEF SUMMARY OF THE INVENTION

The present invention, according to one aspect, is directed to a continuous process of preparing peracetic acid in situ (on-site) and on-demand at a controlled rate to meet the demand of a downstream operation. In one preferred embodiment, peracetic acid in aqueous liquid solution or vapor phase is produced in a continuous pipe-line (tubular) reactor and a distillation column. Pressure in the reactor preferably is maintained sufficiently high to permit operation at higher temperatures than those conventionally employed and thereby prevent the formation of a vapor phase in the reactor. In another embodiment, peracetic acid in aqueous liquid solution or vapor phase is prepared in an apparatus having a continuous pot reactor and distillation column. This configuration is particularly well suited for smaller demand applications, as it offers advantages such as lower capital cost and containing relatively small inventories of the reacting chemicals within the reactor, thereby providing greater safety than in larger-scale operations.

On-site applications of aqueous peracetic acid preferably are monitored continuously to modulate the rate of production to meet the demand of the downstream operation. The availability of a modular, fully automated apparatus for the on-demand production of aqueous peracetic acid at the point of use eliminates the hazards and costs of transporting and storing aqueous peracetic acid.

The process of the present invention has the potential of providing a much safer source of aqueous peracetic acid than that available from existing technologies. This is due in part to the limited inventories of reactants within the reactor, particularly those in the vapor phase. The process offers many advantages for applications requiring disinfection, sanitization, bleaching, delignification, desulfurization, and chemical manufacturing. The peracetic acid finished product, substantially free of residual reactants or impurities, can be produced either as a liquid aqueous solution and metered into any of various applications, or as an aqueous vapor metered directly into a particular application.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION OF THE INVENTION

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope of the present invention.

The present invention will be described hereinafter primarily with reference to the on-site and on-demand production of aqueous peracetic acid at a controlled rate to meet peracetic acid demand in a downstream operation. Of particular commercial importance are the treatment and disinfection of municipal sewage wastewater treatment plant discharges. The production equipment can be sized according to the demand of the downstream operation and preferably is capable of variable production to match low and high daily demand variances. The present invention is useful for the production of aq-PAA for the treatment of a wide variety of water, wastewater, industrial streams, commercial articles, and in the manufacture or purification of chemical compounds and intermediates. Non-limiting examples of other downstream operations include industrial wastewaters, petroleum desulfurization, cooling water circuits, de-inking, cellulose pulp and paper bleaching, textile bleaching, institutional laundries, potable water, process water, recreational and agricultural water, and food and beverage equipment (depicted in FIG. 3). Non-limiting examples of chemical compounds and intermediates manufacture includes the epoxidation and hydroxylation of natural oils used in the plastics, paint and coatings industries, as well as the epoxidation of other natural or synthetic olefins. Other non-limiting examples include the fumigation of e.g., buildings, structures, grains, soils, fruits, vegetables, animals or other articles of commercial value.

In general, the present invention has utility for the treatment of any stream susceptible to treatment by PAA or transformation of a compound by PAA. A "stream susceptible to treatment by PAA" refers to any water, wastewater, or industrial stream for which PAA, with or without additional treatments, would reduce the population of microorganisms (non-limiting examples like protozoa, bacteria, pathogens and viruses) and/or render the stream less toxic, less sulfurous, or otherwise more suitable for or compatible with downstream distribution systems or discharge to a receiving watershed. A "transformation of a compound" refers to any chemical compound that is capable of reacting with PAA to form a new (or purer) chemical species, such as an intermediate or finished product.

In the illustrated embodiments, aqueous peracetic acid is produced from the acid catalyzed reaction between acetic acid (HOAc), and hydrogen peroxide in water in a suitable reaction vessel, distilled off, and applied as either a condensed aqueous solution or as a vapor finished product. The finished product is fed proportionally and directly into the end-use applications as it is produced. The initial phase of the process involves continuously adding the reactants in specific ratios together to produce PAA (also represented as HOOAc) at any concentration, up to and including a steady-state concentration. The rate of PAA formation is proportional to the concentration of acid catalyst, the concentration of each reactant, the temperature of the reaction, and the temperature and pressure of distillation. The overall process chemistry, with sulfuric acid as the acid catalyst, is expressed in Table 1:

TABLE 1 where,
a, b, c, e, f, g, h, i = molar or % weight ratios
xs = excess amount
eq Rxn = equilibrium reaction (reversible)

The stoichiometry of the reaction predicts that 1 mole of acetic acid requires 1 mole of hydrogen peroxide to produce 1 mole of PAA when the reaction is 100% efficient. Since the PAA is in equilibrium with the reactants, then less than stoichiometric amounts of PAA are produced in the reactor. The molar ratios of reactants and yields of eq-PAA are depicted in Table 2 with respect to acetic acid concentration at unity.

TABLE 2

Molar Ratios and Yields of PAA at Equilibrium
With Respect to HOAc at Unity
(In 0.7% w/w catalyst)

| HOAc, mole | $H_2O_2$, mole | PAA, mole |
|---|---|---|
| 1.00 | 0.41 | 0.29 |
| 1.00 | 0.50 | 0.32 |
| 1.00 | 1.00 | 0.44 |
| 1.00 | 1.65 | 0.52 |

The molar ratios of reactants and yields of eq-PAA are depicted in Table 3 with respect to hydrogen peroxide concentration at unity.

TABLE 3

Molar Ratios and Yields of PAA at Equilibrium
With Respect to $H_2O_2$ at Unity
(0.7% catalyst)

| HOAc, mole | $H_2O_2$, mole | PAA, mole |
|---|---|---|
| 0.61 | 1.00 | 0.32 |
| 1.00 | 1.00 | 0.44 |
| 2.00 | 1.00 | 0.66 |
| 2.40 | 1.00 | 0.70 |

Since PAA is distilled off at a variable rate, equilibrium conditions are never met and the reaction shifts or pushes to the right (Table 1). The reactant concentrations or molar ratios may be increased to produce PAA at an increased yield, or reduced to lower the yield. The reactants concentrations are varied according to the rate of production required to meet the application demand.

The reaction between only acetic acid and hydrogen peroxide in water proceeds to equilibrium, although the rate is too slow to be of practical commercial use. Fundamental laws of chemistry also demonstrate that the rates are proportional to the concentration of the primary reactants. However, even at high concentrations, the rate is too slow for practical use.

To increase the rate of PAA formation, an acid such as sulfuric acid is added as a catalyst. When the sulfuric acid concentration is sufficiently high, it is thought that it participates as a reversible super acid (for example Caro's Acid, peroxymonosulfuric acid) or other intermediate since the rate varies with the amount of sulfuric acid and hydrogen peroxide added in the reaction. The rate of PAA formation increases with the concentration of sulfuric acid, as depicted in Table 4. Acid concentrations above 30% are difficult to maintain since the concentrations are limited to the dilution effects from the other reactants. The rates shown illustrate the effect of catalyst and do not limit the scope of the present invention.

TABLE 4

Initial Rates of PAA Formation

| HOAc, mole | $H_2O_2$, mole | Catalyst % $H_2SO_4$ | Initial Rate of PAA Formation mole/min |
|---|---|---|---|
| 1.00 | 1.00 | 0.00 | <0.0001 |
| 1.00 | 1.00 | 0.70 | 0.07 |
| 1.00 | 1.00 | 10.0 | 0.17 |
| 1.00 | 1.00 | 20.0 | 0.26 |
| 1.00 | 1.00 | 30.0 | 0.31 |

A preferred feature of the present invention is to control the rate of formation of PAA by varying the amount of acid catalyst during the reaction. Once the reaction is initiated, the rate may be increased by varying the rate of purge, which raises or lowers the concentration of catalyst in the reactor. Impurities collected in the reaction mixture, for example heavy metals leached from the materials of construction and from the reactants, are also removed in the purge. As the aq-PAA is distilled off, the reaction shifts to the right of the equation (Table 1), producing more PAA. Other catalysts may be used, such as other mineral acid catalysts or a solid phase catalyst, employed either in suspension or in a filter bed, having superacid properties. Particular note is made of sulfated zirconia catalysts optionally containing tungsten and/or phosphate. Pre-mixing the (super)acid catalyst and hydrogen peroxide to enhance Caro's Acid formation may also be used to accelerate PAA formation.

The effect of temperature on the rate of the reaction follows typical Arrhenius behavior. Temperature increases alone are not sufficient to achieve yields of PAA since increasing the temperature above 80° C. accelerates the decomposition of PAA and $H_2O_2$, thereby limiting performance. However, increasing both the temperature and the concentration of sulfuric acid catalyst results in practical rates of reaction. Therefore, adjusting the temperature, from ambient to 60–80° C. provides another method of control to preselect the production rate of PAA. The input of heat energy applied is varied and in proportion to the desired rate of production to meet the application demand.

The rate of production of aq-PAA is further controlled by the pressure and temperature during distillation. A pressure range of 25 to 200 torr (3 to 27 KPa) is preferred, especially from 50 to 100 torr (7 to 13 KPa), within a preferred temperature range of 40 to 60° C. in the distillation column. Therefore, adjusting the pressure and temperature during distillation provides another method of control to preselect the rate of aq-PAA produced. The vacuum and temperature applied is varied in proportion to the desired rate of production required to meet the application demand and to achieve the desired concentration of PAA in the product.

A feature of the present invention relates to safety during the production and handling of PAA. There are two preferred methods used in the present embodiment to generate aq-PAA, one method utilizes a Pipe-Line reactor and the other method uses a Continuous Pot reactor. The method employed depends on the overall rate of aq-PAA required for the end-use applications. Persons skilled in the art recognize that in-process inventories of PAA and its precursors must be kept to minimum levels as part of a hazard risk management program. To reduce the risks inherent in this type of operation, a Continuous Pot reactor may be used for smaller scale operations because the in-process inventories are small and it will often be preferred in such operations because it is less expensive and simpler to operate. A Pipe-Line reactor may be used for any size application by virtue of the minimal in-process inventory (particularly the low volume of vapor) afforded by the use of a short residence time liquid-filled reactor, and it is preferred for all medium-to-large scale operations because of its inherent safety advantages.

Aq-PAA may be produced by either of the reactors previously described. Both methods are illustrated in FIGS. 1 and 2.

Figure 1:
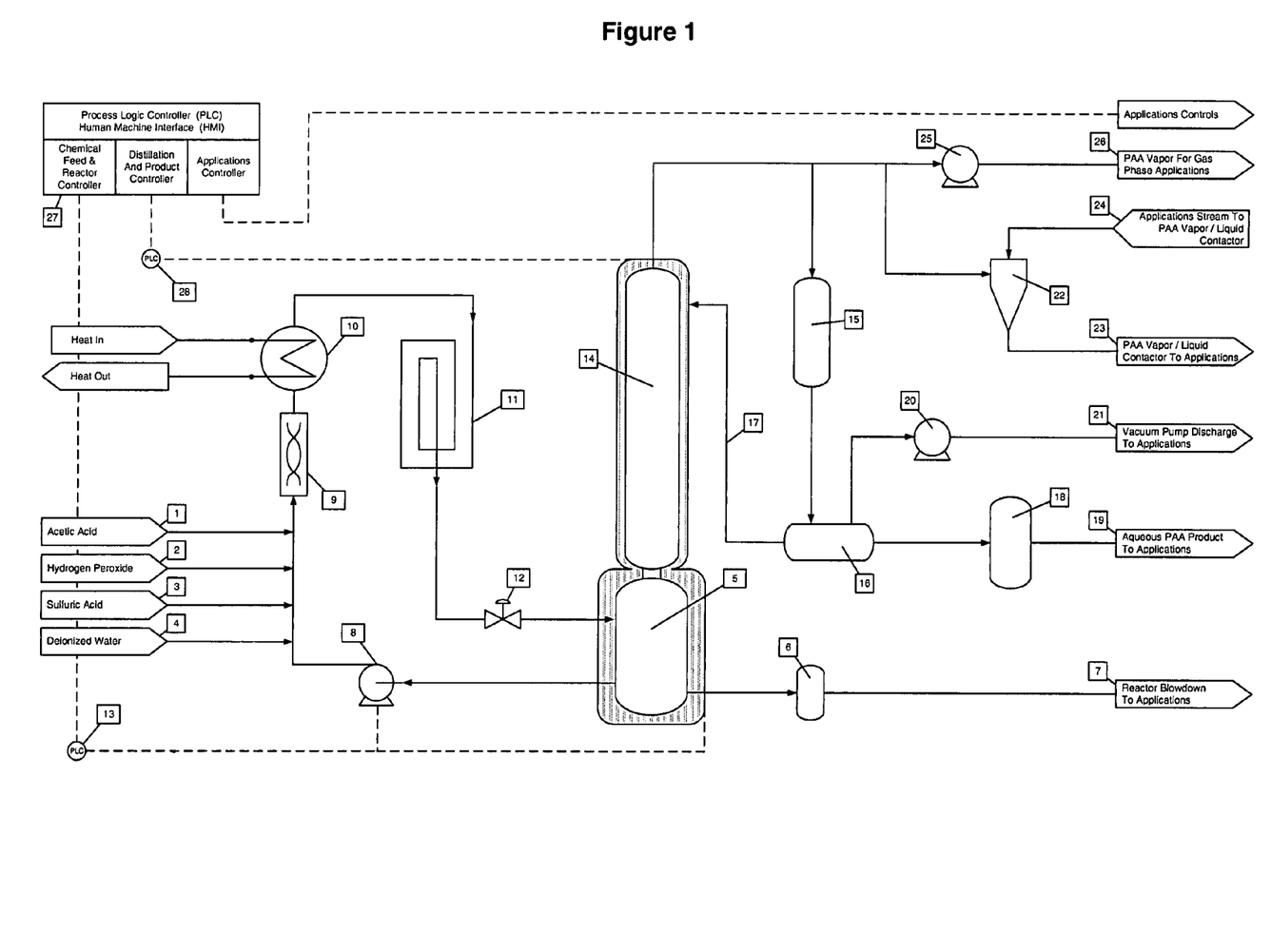
FIG. 1 is process flow diagram for the production of aqueous peracetic acid using a continuous modular apparatus in accordance with one embodiment of the invention.

In the Pipe-Line (PL) reactor depicted in FIG. 1, hydrogen peroxide, acetic acid, sulfuric acid catalyst and water (which are typically added entirely with the hydrogen peroxide and/or acetic acid) are fed to the reactor together with recirculating reaction mixture from the base of the distillation column. Heat for the reaction is provided by a jacket on the PL reactor, which is operated under sufficient pressure (controlled by a back-pressure control valve in the reactor discharge line) to prevent vaporization within the reactor. When the reaction mixture discharges from the reactor into the base of the distillation column, which operates at a lower temperature and pressure, flashing takes place. The vapor rises through the distillation column where it is rectified to give the desired PAA concentration with minimal levels of residual hydrogen peroxide and acetic acid. The liquid recirculates to the PL reactor. The operation of the reactor and associated equipment is modulated to produce sufficient PAA to meet the demands of each application.

Figure 2:
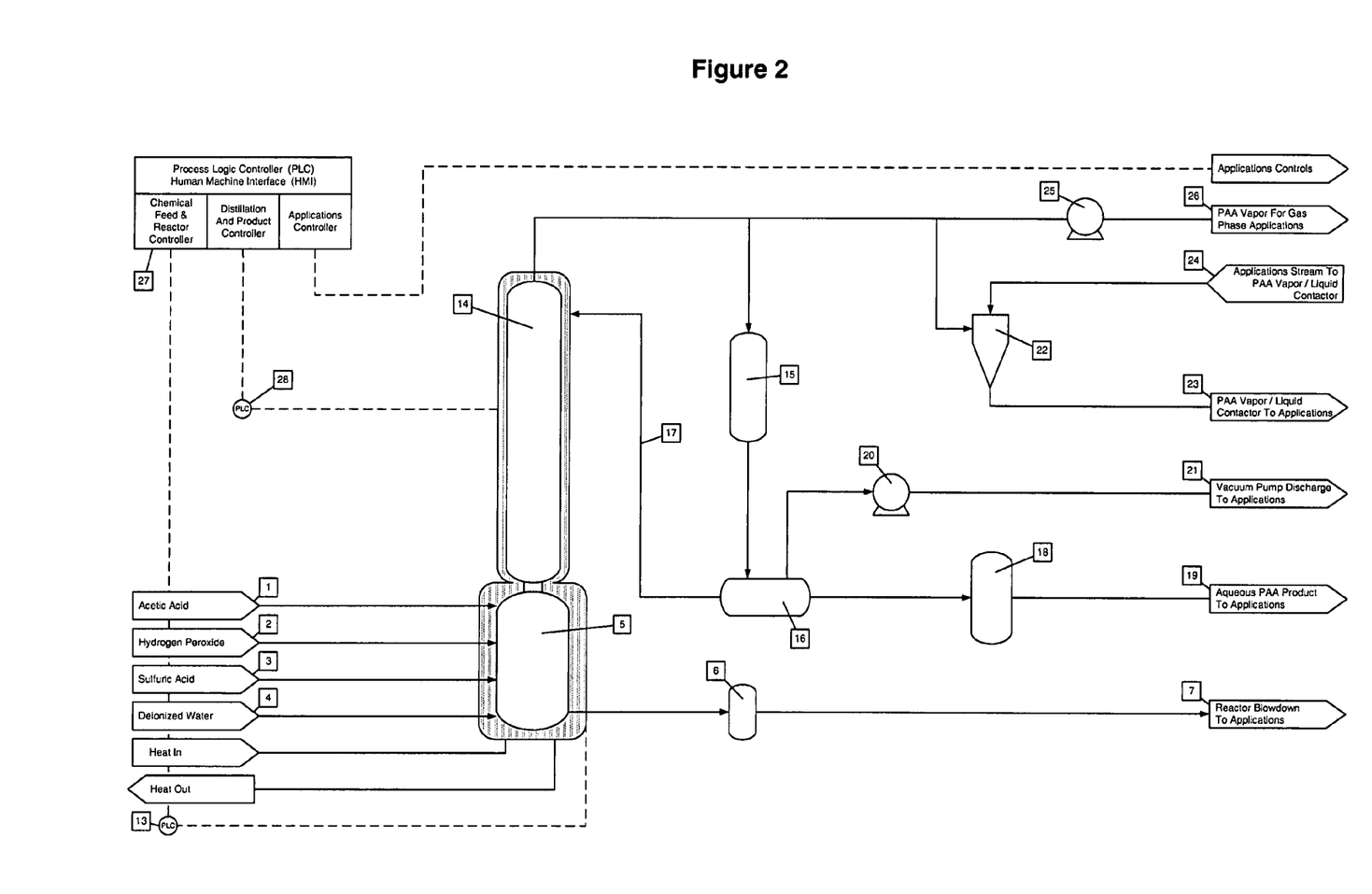
FIG. 2 is process flow diagram for the production of aqueous peracetic acid using a continuous modular apparatus in accordance with the another embodiment of the invention.

The continuous pot (CP) reactor depicted in FIG. 2 is similar to the PL reactor except that the reactants are typically charged to the pot reactor at the base of the distillation column and distillation takes place as a result of heat added by the jacket on the pot reactor using hot water or other heating medium. Reflux is returned to the column to give the desired rectification, while the balance of the vapor is condensed and fed to the application or it is fed directly to the application as a vapor.

Pipe Line Reactor

FIG. 1 illustrates a Pipe-Line (PL) reactor according to a preferred embodiment of the invention. The PL reactor [11] depicted in FIG. 1 operates with greatly reduced volumes of reactants within the reactor than is the case with the CP reactor (FIG. 2), so it is intrinsically safer and particularly well-suited for larger scale operations, though it may be employed for any scale of operation. The raw materials, including acetic acid [1], hydrogen peroxide [2], sulfuric acid [3], and deionized water [4], which is usually or primarily charged with acetic acid and hydrogen peroxide, are charged to the PL reactor [11], which is jacketed [10] and preceded by an in-line mixer [9]. The raw materials are charged at a rate corresponding to the desired production rate. The PL reactor [11] operates at higher temperatures than have heretofore been employed in the production of aqueous peracetic acid and at pressures sufficient to prevent vaporization within the reactor. When the reaction mixture exits the PL reactor [11] through a back-pressure valve [12], it discharges into the base of the distillation column [5], where it flashes at the lower pressure within the column. The vapor rises through the column [14], where it is rectified to give the desired distillate concentration. The constant composition reaction mixture in the base of the column [5] after flashing is re-circulated to the PL reactor [11] where it is combined with fresh reactants. To increase production, the feed rates of all reactants are increased proportionately. Some reduction in purge rate from the base of the column may be needed to increase the catalyst concentration in the reaction mixture to achieve increased production rates and/or the temperature may need to be increased. The residence time in the PL reactor [11] typically ranges from 1 to 30 minutes, preferably 1 to 10 minutes. The reaction temperature within the PL reactor [11] will typically be in the range of 60–80° C. and the pressure will typically be in the range of 500–1500 mm Hg abs.

Distillation Column

A distillation column [14] is mounted directly on top of the base of the distillation column [5] that functions as a surge pot from which the combined liquid leaving the base of the column and the liquid portion of the reactor discharge following flashing is re-circulated to the PL reactor [11] by means of pump [8], while the top of the column is connected to a condenser [15] where the vapor from the top of the column is totally condensed. The distillation column [14] contains one or more theoretical plates. The column may contain as many as 10 or more theoretical plates but in practice usually contains about 3–6 theoretical plates. A portion of the condensate is returned to the top of the column to provide the reflux [17] needed for the rectification of the vapor leaving the pot, while the balance of the distillate is transferred from the distillate receiver [16] to the day drum [18]. The vacuum in the system is provided by a vacuum pump [20] such as a liquid-ring pump using water as a seal liquid. A typical analysis of the distillate is 25% peracetic acid, less than 1% hydrogen peroxide, less than 4% acetic acid, and the balance water. The boiling vapor mixture from the base of the distillation column [5] passes into the bottom of the column [14] at temperatures in the range of 40–60° C., more preferably in the range of 45–55° C., and at pressures in the range of 30–200 torr, more preferably in the range of 50–100 torr.

Optionally, a portion of the vapor from the top of the column [14] may be used without condensation by being educted into a water or air vapor stream to be treated, where the eductor system provides the required vacuum, or it may be withdrawn through a dry vacuum pump; with the balance of the vapor from the top of the column being condensed to provide the reflux needed and a small amount of additional liquid peracetic acid solution that is accumulated in the day drum [18] for use as a liquid and during startup of the system.

Reactor Blowdown

Periodically, a reactor blowdown or purge stream of the mixture in the pot is removed to a level pot [6] to control the level of catalyst and to prevent the accumulation of potentially deleterious levels of contaminants. Some adjustment of the purge rate may also be needed when production rates are to be changed. In many cases, it may be feasible to add the purged mixture to end-use application, which avoids a minor wasted disposal requirement. In other cases, it may be necessary to discharge the purge stream to the sewer following neutralization.

Vacuum System and Vent

Vacuum can be provided by a liquid-ring vacuum pump [20] using water on a once-through basis as the seal liquid. If the end use of the PAA is for wastewater treatment, that water may be used as the seal liquid. All condensibles remaining in the vent from the condenser will be absorbed in the water used as the seal liquid. The level of vacuum is controlled by admitting air to the inlet of the vacuum pump. The vent from the vacuum pump, substantially free of any organic contaminants, is discharged to the atmosphere.

Alternatively, for some applications such as wastewater treatment, the vacuum may be provided by an eductor system [22] using the water to be treated as the motive fluid. Here too the air in the flow to the eductor system will either dissolve in the water to be treated or it will separate from the water substantially free of any organic contaminants. Alternatively, a dry vacuum pump [25] may be used where the vapor is to be used for gas phase applications [26], for example to disinfect soil, fruits or vegetables.

Condenser

A condenser [15] using chilled water as a coolant condenses all or a portion of the vapor from the top of the column [14]. The condensate drains into the distillate receiver [16], from which part of it is pumped to the top of the column as reflux [17] and the balance is pumped to the day drum [18], from which it is pumped to the end-use application as needed or accumulated for supplementary uses and startup following a shutdown.

Controller

Figure 3:
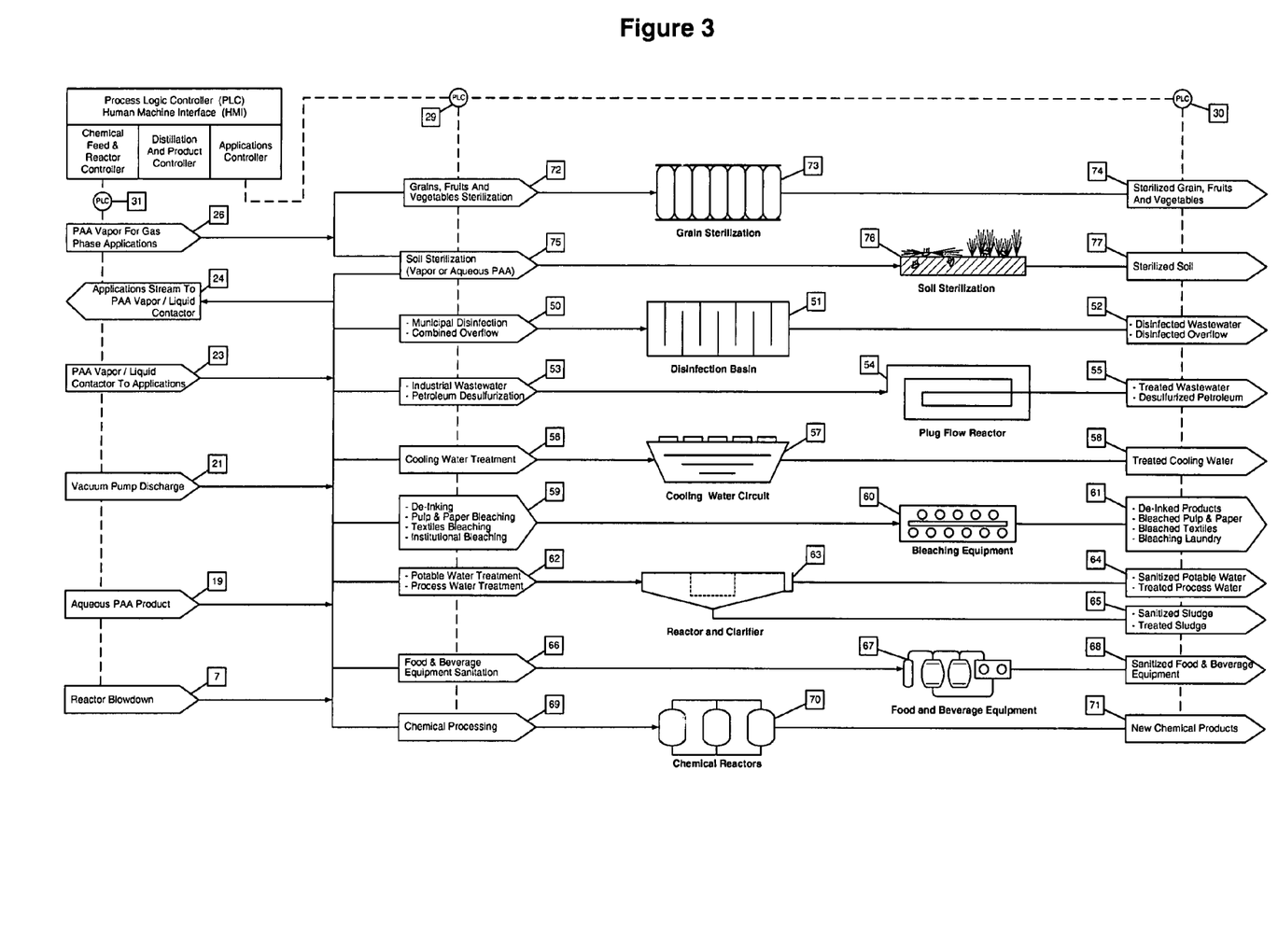
FIG. 3 schematically illustrates a variety of potential end uses of aqueous peracetic acid produced on-site and on-demand in accordance with the present invention.

The process and applications preferably are managed by a computerized controller [27] where input/output (I/O) channels [13], [28], [29], [30], and [31], shown in FIGS. 1, 2, and 3, send and receive information to the process modules. The process modules include the chemical precursors and reactors, distillation equipment and PAA products, and applications. The controller comprises a computer or PLC and human machine interface (HMI) [27] where the operation of the entire process is maintained. The production of aq-PAA is modulated to a desired rate within the design specifications of each process model.

Continuous Pot Reactor

The Continuous Pot (CP) embodiment illustrated in FIG. 2 is particularly well suited for smaller production rates. In this example, the precursor chemicals include acetic acid [1], hydrogen peroxide [2], sulfuric acid [3], and deionized water [4], which is usually or primarily added with the hydrogen peroxide and/or acetic acid. Initially, the base of the distillation column [5], which functions as the CP reactor, is charged with the amounts of each chemical required to approximate the anticipated steady state composition of the pot. Vacuum is applied at the desired level and pot contents are heated to the normal reaction temperature. The feeding of hydrogen peroxide, acetic acid and sulfuric acid (usually premixed with the acetic acid) are then started. Heat is applied to the reactor by low pressure steam or hot water circulated through a jacket, or by an electric pot heater to achieve the desired constant rate of vaporization which will maintain the level in the pot while simultaneously removing a small liquid purge stream or blowdown from the pot.

A distillation column [14] that provides at least 3–6 theoretical plates is mounted directly on top of the CP reactor [5], while the top of the column is connected to a condenser [15] where the vapor from the top of the column is totally condensed. A portion of the condensate is returned to the top of the column to provide the reflux [17] needed for the rectification of the vapor leaving the CP reactor [5], while the balance of the distillate is transferred from the distillate receiver [16] to the day drum [18]. A typical analysis of the distillate is 25% peracetic acid, less than 1% hydrogen peroxide, less than 4% acetic acid and the balance water. The boiling vapor mixture from the pot passes into the bottom of the column [14] at temperatures in the range of 40–60° C., more preferably in the range of 45–55° C., and at pressures in the range of 30–200 torr, more preferably in the range of 50–100 torr.

As in the preferred embodiment of FIG. 1, a portion of the vapor from the top of the column may be used without condensation by being educted into a water stream to be treated, where the eductor system provides the required vacuum, or it may be withdrawn through a dry vacuum pump; with the balance of the vapor from the top of the column being condensed to provide the reflux needed and a small amount of additional liquid peracetic acid solution.

Periodically, a reactor blowdown or purge stream of the mixture in the CP reactor [5] is removed to a level pot [6] to control the level of catalyst and to prevent the accumulation of potentially deleterious levels of contaminants. Some adjustment of the purge rate may also be needed when production rates are to be changed. In many cases, it may be feasible to add the purged mixture to end-use application, which avoids a minor wasted disposal requirement. In other cases, it may be necessary to discharge the purge stream to the sewer following neutralization.

Other features of the CP reactor embodiment of FIG. 2, including the vacuum pump [20], eductor system [22], controller [27], and other components, may be as described above with reference to the PL embodiment of FIG. 1.

End-Use Applications

The present invention is described with reference to the in situ and on-demand production of aqueous peracetic acid at a rate proportional to the subsequent end use applications [50] through [77], depicted in FIG. 3. Of particular commercial importance is the treatment and disinfection of municipal sewage wastewater treatment plant (WWTP) discharges. The present invention is also useful for the production of aq-PAA and treatment of a wide variety of water, wastewater, industrial effluents, food and beverage, and in the manufacture of chemical compounds and intermediates. Non-limiting examples of end use applications are discussed by way of examples for each of the following industries:

| |
|---|
| Municipal Wastewater Treatment [50] |
|     Municipal Wastewater Disinfection |
|     Combined Sewer Overflow Disinfection |
| Industrial [53] |
|     Industrial Wastewater Treatment |
|     Petroleum Desulfurization |
| Cooling Water Treatment [56] |
| Bleaching [59] |
|     De-Inking |
|     Pulp and Paper Bleaching |
|     Textiles Bleaching |
|     Institutional Laundries Bleaching |
| Water Treatment [62] |
|     Potable Water Disinfection |
|     Process Water Sanitizing |
| Food And Beverage Equipment Sanitizing [66] |
| Chemical Processing [69] |

Applications using PAA traditionally use equilibrium PAA where significant amounts of the reactants (namely $H_2O_2$, HOAc, and sulfuric acid) remain in the equilibrium product. The applications listed above generally operate at a much lower cost using aq-PAA compared to eq-PAA since all precursor chemicals are reacted into aq-PAA, while the sulfuric acid catalyst is purged from the reactor. Operating costs are lowered further where the precursor chemicals are delivered to the customer in bulk packaging, for example in truckload quantities, where aq-PAA is produced on-site at bulk chemical prices. By comparison, currently eq-PAA must be delivered in packaged quantities less than 300 gallons, which greatly increases the chemical prices, handling requirements, and operating costs.

Municipal Wastewater Disinfection [50] (cf. Disinfection Basin [51])

Perhaps the largest application of aq-PAA is for the disinfection of municipal wastewater effluents [50] as an alternative to, e.g., chlorine based disinfection. Aq-PAA is applied to the wastewater final stage at a concentration usually ranging from about 0.5 to 25 mg/L, more preferably from about 5 to 15 mg/L, to achieve disinfection standards for discharge to a receiving watershed. In older construction specifications, the aq-PAA may be applied directly into an existing disinfection basin [51] with no additional capital improvements, a non-limiting example is a typical basin exhibiting plug flow characteristics previously used for conventional chlorine based disinfection processes. Although the size of the basin originally used for chlorine disinfection is based on a minimum 30 min. contact time, the time required for aq-PAA disinfection is in the order of 5 to 7 min. The extra capacity of an existing disinfection basin does not limit the performance of aq-PAA. In new construction specifications, a disinfection basin employing aq-PAA requires a much smaller footprint, less volume, and less retention time compared to traditional chlorination. Hence, the capital and operating cost are further reduced using aq-PAA disinfection.

Environmental regulations and discharge permits promulgated in the Clean Water Act of 1972 and later amendments, restrict chlorine residuals in wastewater discharges to a receiving watershed. To meet these guidelines, dechlorination is required to eliminate the residual chlorine. Typical dechlorination processes add gaseous sulfur dioxide or sodium bisulfite solutions into a dechlorination basin prior to discharge. Disinfection basins have been modified and constructed to include both chlorination and dechlorination chambers. The use of aq-PAA disinfection does not require any additional treatment prior to discharge. Any residual aq-PAA will transform to acetic acid, water, and oxygen with no significant impact on any discharge parameters, non-limiting examples of discharge parameters include TOC, COD, BOD, and toxicity.

A disinfection basin [51] using (but not limited to) a typical oxidation basin design is well suited for aq-PAA applications. The disinfection is monitored and controlled by a PLC and electronic sensors located throughout the disinfection process, non-limiting controls include Oxidation-Reduction Potential (ORP) and Ion Selective Probes (ISP). The performance of the application is evaluated by the PLC and the production and quality of aq-PAA is modulated to meet the demands. Depending on the extent of automation at the site of use, the user's controller may be interfaced with the aq-PAA process PLC to reduce redundant controls and sensors.

Combined Sever Overflow [50] (cf. Disinfection Chamber [51])

Throughout the modern world, municipal wastewater treatment plants (WWTPs) have the authority to bypass incoming sewage during times of high storm activity and flooding to protect the facility from hydraulic washout, termed Combined Sewer Overflow (CSO). During a bypass event, discharge permit limits and reportable quantities may be exceeded, including no disinfection, without violation or penalty. However, new regulations promulgated by Federal agencies prohibit the discharge of CSO without disinfection. As a disinfection agent, aq-PAA is also cost effective compared to conventional chlorination and dechlorination practices, including but not limited to, sodium hypochlorite (termed "hypochlorite") and sodium bisulfite (termed "bisulfite") processes, respectively.

Hypochlorite based disinfection programs require large chemical storage tanks and large disinfection chambers to meet the treatment requirements during a CSO event. During a long period between CSO events, for example greater than three months, the stored hypochlorite will loose significant amounts of active available chlorine. The half-life of hypochlorite can be less than one year which suggests longer storage periods will not have adequate amounts of active chlorine available during a CSO event. Tanks with high capacities must be installed as a contingency and poses further safety concerns and hazard risk profiles. The size of the chlorination and dechlorination disinfection chambers will depend on the CSO incursion rate expected and the minimum 30 min. contact time required.

The advantage of the present invention over existing technologies is aq-PAA is produced in situ and available at full strength and on-demand regardless of the storage or shelf life of the precursor chemicals. For example, only $H_2O_2$ may be considered to have a limiting shelf life, however, <1% degradation per year is expected and any losses will have no impact on the production or use of aq-PAA when needed.

A typical disinfection basin [51] using (but not limited to) a typical oxidation ditch design is well suited for aq-PAA applications. The disinfection is monitored and controlled by a PLC and electronic sensors located throughout the disinfection process, non-limiting controls include ORP and ISP. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Industrial Wastewater [53] (cf. Plug Flow Reactor [54])

Many types of industrial wastewaters [53] are not amenable to disposal in conventional biological wastewater treatment plants due to high loading characteristics, for example TOC, COD, and BOD, and toxic properties, for example refractory and phenolic compounds. Pretreatment applications include chemical oxidation to destroy the precursors responsible for toxicity and to transform refractory compounds into products easily assimilated in the biological treatment process [55]. In cases where a selective chemical oxidizer is required, aq-PAA oxidizes substrates that are not otherwise oxidized by other oxidation programs. Aq-PAA is most efficient when used in concentration ranges from about 10 to 250 mg/L for typical applications and up to about 100 to 10,000 mg/L for highly refractory compounds.

A plug flow reactor design [54] comprising a given length of pipe, or similar conduit, but not limited to, is well suited to pretreat industrial wastewaters. The industrial wastewater process is monitored and controlled by a PLC and electronic sensors located throughout the industrial wastewater treatment process, non-limiting controls include ORP, ISP, pH, and automatic titrators. The performance of the application is evaluated by the PLC and the production and quality of aq-PAA is modulated to meet the demands. Depending on the extent of automation at the site of use, the user's controller may be interfaced with the aq-PAA process PLC to reduce redundant controls and sensors.

Petroleum Desulfurization [53] (cf. Plug Flow Reactor [54])

Worldwide guidelines requiring low sulfur content fuels has promoted the application of aq-PAA for the oxidation and removal of sulfur compounds to meet the newest standards. Petroleum desulfurization by oxidation of sulfides and thiols (mercaptans) uses aq-PAA at concentrations ranging from 1 to 5,000 mg/L, more preferably 50 to 500 mg/L, in finished gasoline, kerosene, and diesel fuels, without limitation.

A plug flow reactor design [54] comprising a given length of pipe, or similar conduit, but not limited to, is well suited to pretreat petroleum products. The desulfurization process is monitored and controlled by a PLC and electronic sensors located throughout the desulfurization process, non-limiting controls include ISP's and automatic inline sulfur analyzers. The performance of the application is evaluated by the PLC and the production and quality of aq-PAA is modulated to meet the demands. Depending on the extent of automation at the site of use, the user's controller may be interfaced with the aq-PAA process PLC to reduce redundant controls and sensors.

Cooling Water [56] (cf. Cooling Water Circuit [57])

Cooling water circuits [56] used throughout manufacturing, industrial, and electrical generation plants suffer greatly from the effects of biological growth and microorganisms. Aq-PAA is effective for controlling biological growth and limiting the deleterious effects caused in cooling water circuits. Aq-PAA is effective at concentrations from 0.5 to 100 mg/L, more preferably 2 to 25 mg/L, in most applications. Aq-PAA may be applied directly to the cooling water circuit without any capital improvements to existing facilities.

The cooling water quality is monitored and controlled by a PLC and electronic sensors located throughout the cooling water circuit, non-limiting controls include ORP and ISP. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

De-Inking [59] (cf. Bleaching Equipment [60])

The recycling of paper products requires that the resulting pulp be free of the colors contained in the original material. Aq-PAA is particularly effective for the de-inking [53] of these products. Aq-PAA is effective at concentrations from 1 to 5,000 mg/L, more preferably 100 to 1,000 mg/L, in most applications. Aq-PAA may be applied directly to the deinking processes with little or no capital improvements to existing facilities.

The deinking process is monitored by a PLC and electronic sensors located throughout the deinking process, non-limiting controls include ORP, ISP, and brightness measurements. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Pulp And Paper Bleaching And Delignification [59] (Bleaching Equipment [60])

The bleaching and delignification of cellulose pulp [59] yields better results using aq-PAA compared to conventional chlorine or hydrogen peroxide based processes. Aq-PAA is effective from 100 to 1,000 mg/L and up to 1 to 5% concentrations, depending on the application. Aq-PAA may be applied directly to the manufacturing circuit in conventional bleaching baths without extensive capital improvements to existing facilities.

The bleaching and delignification processes are monitored and controlled by a PLC and electronic sensors located throughout the bleaching and delignification processes, non-limiting controls include ORP, ISP, automatic titrators, and brightness measurements. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Textiles [59] (cf. Bleaching Equipment [60])

The bleaching of textiles [59] demonstrates better properties using aq-PAA compared to conventional chlorine or hydrogen peroxide based processes. Aq-PAA is effective from about 100 to 1,000 mg/L and up to about 1 to 5% concentrations, depending on the application. Aq-PAA may be applied directly to the manufacturing circuit in conventional equipment without extensive capital improvements to existing facilities.

The textile processes are monitored and controlled by a PLC and electronic sensors located throughout the textile processes, non-limiting controls include ORP, ISP, automatic titrators, and brightness measurements. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Institutional Laundries [59] (cf. Bleaching Equipment [60])

The color safe bleaching of clothing and other fabrics in institutional laundries [59] demonstrates better properties using aq-PAA compared to conventional chlorine or peroxide based processes. Aq-PAA is effective from about 50 to 10,000 mg/L, more preferably from about 100 to 500 mg/L, depending on the items being laundered.

The laundry process is monitored and controlled by a PLC and electronic sensors located throughout the process, non-limiting controls include ORP, ISP, and brightness measurements. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Potable Water Treatment [62] (cf. Reactor And Clarifier [63])

There is considerable momentum, partially from the US Environmental Protection Agency (EPA), to promote total free chlorine (TFC) disinfection programs in potable water [62]. Aq-PAA is effective for disinfection during contact treatment [63], and equally important, as a post treatment disinfectant throughout the distribution system to the point-of-use (POU) [64], or at the "tap." Aq-PAA is effective at concentrations from about 0.5 to 5 mg/L during contact treatment and positive residuals of about 0.25 to 2 mg/L in the distribution network. Aq-PAA may be applied directly to existing water intake, storage, treatment and distribution systems without extensive capital improvements. The sludge produced [65] may also be disinfected.

The potable water process is monitored and controlled by a PLC and electronic sensors located throughout the process [63], non-limiting controls include ORP, pH, and ISP measurements. The performance of the application is evaluated by the PLC and the production and quality of aq-PAA is modulated to meet the demands.

Potable Water Distribution Network [64]

Following the treatment of potable water, the residual aq-PAA in the distribution network and piping is monitored and controlled by a PLC and electronic sensors, non-limiting controls include ORP, pH, and ISP measurements. Data from the distribution network can be transmitted back to the PLC where the performance of the distribution system is evaluated and the production and quality of aq-PAA is modulated to meet the demands. Depending on the extent of automation at the site of use, the user's controllers may be interfaced with the aq-PAA process PLC without redundant controls and sensors.

Process Water Treatment [62] (cf. Reactor And Clarifier [63])

Process waters [62] obtained from surface impoundments, for example rivers and lakes, pose a particular problem to the facility operations due to colloidal suspensions, microorganisms, and plant matter. The oxidation and disinfection properties of aq-PAA make it particularly useful in achieving a clarified product with minimal additional water treatment additives. Depending on the initial quality of the water, aq-PAA is effective from about 0.5 to 50 mg/L, more preferably from about 5 to 25 mg/L. Aq-PAA may be applied directly to existing process water circuits without extensive capital improvements.

The quality of process water is monitored and controlled by a PLC and electronic sensors located throughout the process, non-limiting controls include ORP, pH, and ISP. The performance of the application is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Food, Beverage and Fermentation Equipment Sanitation [66] (cf. Food and Beverage Equipment [67])

Chlorine based sanitizing programs have been traditionally employed in the food, beverage and fermentation industries [66], non-limiting examples include food processing plants, fruits and vegetables conveyance, and processing vats including alcoholic beverages, soft drink production and chemicals produced by fermentation [67]. Eq-PAA was introduced as an effective alternative, however, it is known that the active sanitizing ingredient in eq-PAA is the PAA. Production of aq-PAA in situ on-demand is more cost effective and safer to handle than conventional eq-PAA. Depending on the initial contamination of the equipment, aq-PAA is effective from 0.5 to 1,000 mg/L, more preferably 100 to 250 mg/L. Aq-PAA may be applied directly to existing equipment without extensive capital improvements.

Sanitizing processes are monitored and controlled by a PLC and electronic sensors located throughout the process [67], non-limiting controls include ORP and ISP measurements. The performance of the application [68] is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Chemical Processing [69] (cf. Chemical Reactors [70])

Chemical compounds and intermediates manufacture includes, but is not limited to, the use of aq-PAA for oxidations such as epoxidation and hydroxylation of olefinic materials such as natural oils, hydrocarbons, etc. Traditionally, these epoxides and other oxidation products are used as is or as reactive intermediates in the paint and coatings, adhesives, plastic additives, lube and fuel additives, personal care, and oil field processing industries. The epoxidation and hydroxylation of olefinic compounds historically uses eq-PAA, where the remaining $H_2O_2$, HOAc and sulfuric acid are not utilized and therefore wasted, or it is performed using the on-site production of the PAA from these reactants. But, in using epoxidation chemistry it is very difficult to stop the formation of by-products that result from the reaction of the sulfuric acid and even the acetic acid with the epoxidation or oxidation product. A preferred feature of the present invention is producing aq-PAA where all of the reactants are transformed into aq-PAA with no significant reactants lost or wasted. Therefore, the present invention produces PAA at substantially less cost per active unit and produces final products of substantially lower costs compared to eq-PAA. The availability of aq-PAA produced in accordance with this invention may be used in various chemical processing of product synthesized only from aq-PAA [71]. As will be appreciated by persons skilled in the art, the reaction stoichiometry and particulars of the reaction equipment will dependent on such factors as the type of synthesis and product specifications.

The chemical manufacturing processes are monitored by a PLC including I/O channels from the manufacturing equipment. The performance of the application [71] is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

Grain Sterilization [72] (cf. Grain Sterilization [73])

Vaporous PAA may be used for grain sterilization [72] as an alternative to present gaseous methyl bromide sterilization technology. The aq-PAA can be applied directly as a gaseous product [26], non-limiting examples include to grain silos or other stowage [73].

The performance of the application [74] is evaluated by the PLC and the production and quality of aq-PAA is modulated to meet the demands. Depending on the extent of automation at the site of use, the user's existing controller may be interfaced with the aq-PAA process PLC to reduce control redundant controls and sensors.

Soil Sterilization [75] (cf. Soil Sterilization [76])

Another embodiment of the invention is the application of vapor PAA for soil sterilization [75] as an alternative to other soil sterilization technologies. The aq-PAA can be applied as a gaseous product [26] directly into soil strata [76]. In some applications, aq-PAA may be applied also as an aqueous solution [75].

The performance of the application [77] is evaluated by the PLC and the production and quality of aq-PAA is modulated to meet the demands. Depending on the extent of automation at the site of use, the user's existing controller may be interfaced with the aq-PAA process PLC to reduce redundant controls and sensors.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

We claim:

1. A continuous process for producing peracetic acid on-site and on-demand at a controlled rate compatible with the demand for peracetic acid in a downstream operation, the process comprising:
   (a) feeding acetic acid, hydrogen peroxide, an acid catalyst, and water into a tubular reactor to form a reaction medium;
   (b) feeding vapor from the reaction medium into the base of a distillation column, from which product is removed as distillate or effluent; and
   (c) controlling the rate of peracetic acid discharged in an effluent stream from the distillation column so that the rate at which peracetic acid is produced is compatible with the demand for peracetic acid in the downstream operation;
   wherein reaction between the acetic acid and hydrogen peroxide occurs primarily in the tubular reactor.

2. The process of claim 1 wherein the effluent stream comprises peracetic acid in an aqueous solution.

3. The process of claim 1 wherein the effluent stream comprises peracetic acid in a vapor phase.

4. The process of claim 1 wherein the rate of production of peracetic acid is controlled by increasing or decreasing catalyst concentration by purging a portion of the reaction medium from a recirculating line to the tubular reactor prior to introducing fresh acetic acid, hydrogen peroxide, catalyst, and water.

5. The process of claim 1 wherein the rate of production of peracetic acid is controlled by increasing or decreasing thermal energy input into the tubular reactor.

6. The process of claim 1 wherein the rate of production of peracetic acid is controlled by increasing or decreasing back-pressure in the tubular reactor to prevent the formation of a vapor phase.

7. The process of claim 6 wherein the rate of production of peracetic acid is controlled by controlling the temperature in the tubular reactor.

8. The process of claim 1 wherein the catalyst is selected from the group consisting of sulfuric acid, phosphoric acid, phosphonic acid, sulfonic acid, a superacid containing at least one of sulfuric acid, tungsten, and phosphate, a superacid containing a sulfated zirconia compound containing at least one of tungsten and phosphate, and mixtures thereof.

9. The process of claim 1 wherein the hydrogen peroxide is pre-mixed with the acid catalyst, and thereafter contacted with the acetic acid to form peracetic acid.

10. The process of claim 1 wherein a superacid catalyst is calcined into a support containing at least one of solid silica and zirconia, and wherein said support is placed into a column through which the hydrogen peroxide, a mixture of peroxyacid precursors, or both, are passed.

11. The process of claim 1 wherein a portion of the reaction medium is purged from a recirculating line prior to the introduction of fresh acetic acid, hydrogen peroxide, catalyst, and water to prevent buildup of trace metal contaminants.

12. The process of claim 11 wherein excess acids or impurities collected in the reactor are discharged to the downstream operation.

13. The process of claim 1 wherein vacuum in the system is created by a vacuum pump connected to the discharge end of the condenser in which the distillate is condensed.

14. The process of claim 13 wherein the vacuum pump is a liquid-ring vacuum pump and wherein seal liquid discharge and/or the vacuum discharge from the vacuum pump is captured and fed into the downstream operation.

15. The process of claim 1 wherein a plurality of tubular or plug flow reactors and distillation columns are operated in parallel.

16. The process of claim 1 wherein the molar ratio of hydrogen peroxide to acetic acid fed to the reaction system is from about 0.5:1 to about 10:1.

17. The process of claim 16 wherein the molar ratio of hydrogen peroxide to acetic acid is from about 1:1 to about 5:1.

18. The process of claim 17 wherein the molar ratio of hydrogen peroxide to acetic acid is from about 1:1 to about 3:1.

19. The process of claim 1 wherein a mineral acid catalyst is premixed with acetic acid to achieve a concentration in the reactor of from about 1 to about 50 wt %.

20. The process of claim 19 wherein the mineral acid catalyst is premixed with acetic acid to achieve a concentration in the reactor of from about 5 to 20 wt %.

21. The process of claim 1 wherein the pressure in the distillation column is from about 3 to 27 KPa.

22. The process of claim 21 wherein the pressure in the distillation column is from about 5 to 17 KPa.

23. The process of claim 5 wherein the temperature in the tubular reactor ranges from about 40 to about 100° C.

24. The process of claim 23 wherein the temperature in the tubular reactor ranges from about 60 to about 80° C.

25. The process of claim 1 wherein the downstream operation is disinfection of municipal wastewater treatment plant effluent, and wherein the controlled rate of peracetic acid discharge is defined by a peracetic acid-to-wastewater effluent ratio of from about 0.5 to about 100 mg/L.

26. The process of claim 25 wherein the peracetic acid-to-wastewater effluent ratio is from about 3 to about 25 mg/L.

27. The process of claim 1 wherein the downstream operation is disinfection of combined sewer overflow, and wherein the controlled rate of peracetic acid discharge is defined by a peracetic acid-to-combined sewer overflow ratio of from about 0.1 to about 500 mg/L.

28. The process of claim 27 wherein the peracetic acid-to-combined sewer overflow ratio is from about 5 to about 100 mg/L.

29. The process of claim 1 wherein the downstream operation is reducing the concentration of undesirable organic and inorganic substances in an influent or effluent industrial wastewater stream, and wherein the controlled rate of peracetic acid discharge is defined by a peracetic acid-to-industrial wastewater ratio of from about 0.1 to about 100,000 mg/L.

30. The process of claim 29 wherein the peracetic acid-to-industrial wastewater ratio is from about 10 to about 1,000 mg/L.

31. The process of claim 1 wherein the downstream operation is treating petroleum products to oxidize sulfides, mercaptans, and similar analogues, and wherein the controlled rate of peracetic acid discharge is defined by a peracetic acid-to-petroleum products ratio of about 1 to about 5,000 mg/L.

32. The process of claim 31 wherein the peracetic acid-to-petroleum products ratio is from about 50 to about 500 mg/L.

33. The process of claim 1 wherein the downstream operation is disinfection of cooling waters, and wherein the controlled rate of peracetic acid discharge is defined by a peracetic acid-to-cooling water ratio of about 0.5 to 100 mg/L.

34. The process of claim 33 wherein the peracetic acid-to-cooling water ratio is from about 2 to about 25 mg/L.

35. The process of claim 1 wherein the downstream operation is deinking a medium containing recycled paper products, and wherein the controlled rate of peracetic acid discharge is defined by a peracetic acid-to-recycled paper products medium ratio of about 1 to about 5,000 mg/L.

36. The process of claim 35 wherein the peracetic acid-to-recycled paper products medium ratio is from about 50 to about 1,000 mg/L.

37. The process of claim 1 wherein the downstream operation is at least one of bleaching and delignifying a pulp or paper product stream, and wherein the controlled rate of peracetic acid discharge is defined by a peracetic acid-to-pulp or paper products stream ratio of from about 10 to about 100,000 mg/L.

38. The process of claim 37 wherein the peracetic acid-to-pulp or paper products stream ratio is from about 100 to about 10,000 mg/L.

39. The process of claim 1 wherein the downstream operation is bleaching a stream containing textiles, and wherein the controlled rate of peracetic acid discharge is defined by a peracetic acid-to-textile stream ratio of about 10 to about 10,000 mg/L.

40. The process of claim 39 wherein the peracetic acid-to-textile stream ratio is from about 50 to about 1,000 mg/L.

41. The process of claim 1 wherein the downstream operation is bleaching a stream containing institutional laundries, and wherein the controlled rate of peracetic acid discharge is defined by a peracetic acid-to-institutional laundries stream ratio of from about 50 to about 10,000 mg/L.

42. The process of claim 41 wherein the peracetic acid-to-institutional laundries stream ratio is from about 100 to about 1,000 mg/L.

43. The process of claim 1 wherein the downstream operation is treating and disinfecting potable water, and wherein the controlled rate of peracetic acid discharge is defined by a peracetic acid-to-potable water ratio of from about 0.5 to about 50 mg/L.

44. The process of claim 1 wherein the downstream operation is treating and disinfecting process water, and wherein the controlled rate of peracetic acid discharge is defined by a peracetic acid-to-process water ratio of from about 0.5 to about 1,000 mg/L.

45. The process of claim 44 wherein the peracetic acid-to-process water ratio is from about 3 to about 100 mg/L.

46. The process of claim 1 wherein the downstream operation is disinfecting and sanitizing food and beverage handling equipment, and wherein the controlled rate of peracetic acid discharge is defined by a peracetic acid-to-disinfecting and sanitizing stream ratio of from about 0.5 to about 1,000 mg/L.

47. The process of claim 46 wherein the peracetic acid-to-disinfecting and sanitizing stream ratio is from about 3 to about 100 mg/L.

48. The process of claim 1 wherein the downstream operation is epoxidizing and hydroxylating at least one of alkyls, oils, and fats in a chemical processing stream, and wherein the controlled rate of peracetic acid discharge is defined by a molar ratio of about 0.5:1 to about 5:1 of peracetic acid to alkyl, oils and fats.

49. The process of claim 48 wherein the molar ratio is from about 1:1 to about 2:1 of peracetic acid to alkyl, oils and fats.

50. The process of claim 1 wherein the rate of production of peracetic acid is controlled by an electronic or mechanical device connected to the downstream operation, wherein a signal is sent a controller to increase or decrease the rate of production of peracetic acid.

51. The process of claim 43 wherein the peracetic acid-to-potable water ratio is from about 3 to about 50 mg/L.

* * * * *